United States Patent [19]

Boelke et al.

[11] Patent Number: 5,486,530
[45] Date of Patent: Jan. 23, 1996

[54] USE OF TORASEMIDE FOR THE TREATMENT OF BRAIN OEDEMAS

[75] Inventors: Tim Boelke; Lothar Kling, both of Mannheim; Reinhard Koenig, Grunstadt, all of Germany

[73] Assignee: Boehringer Mannheim GmbH, Mannheim, Germany

[21] Appl. No.: 380,323

[22] Filed: Jan. 30, 1995

Related U.S. Application Data

[63] Continuation of Ser. No. 133,160, Oct. 21, 1993, abandoned.

[30] Foreign Application Priority Data

Apr. 27, 1991 [DE] Germany .................. 41 13 820.1

[51] Int. Cl.[6] .................................................. A61K 31/44
[52] U.S. Cl. .................................................. 514/347
[58] Field of Search ................................. 514/347

[56] References Cited

U.S. PATENT DOCUMENTS

| 4,018,929 | 4/1977 | Delarge et al. | 514/347 |
| 4,861,786 | 8/1989 | Demmer et al. | 514/347 |
| 5,166,162 | 11/1992 | Masereel et al. | 514/339 |

OTHER PUBLICATIONS

P. A. Tornheim et al., Neurosurgery, vol. 4, No. 1 (1979) pp. 48–52.

H. A. Friedel et al., Drugs 41(1): 81–103 (1991).

*Primary Examiner*—Raymond Henley, III
*Attorney, Agent, or Firm*—Nikaido, Marmelstein, Murray & Oram

[57] ABSTRACT

Use of torasemide for the treatment of brain edemas and orally and parenterally administerable torasemide.

8 Claims, 5 Drawing Sheets

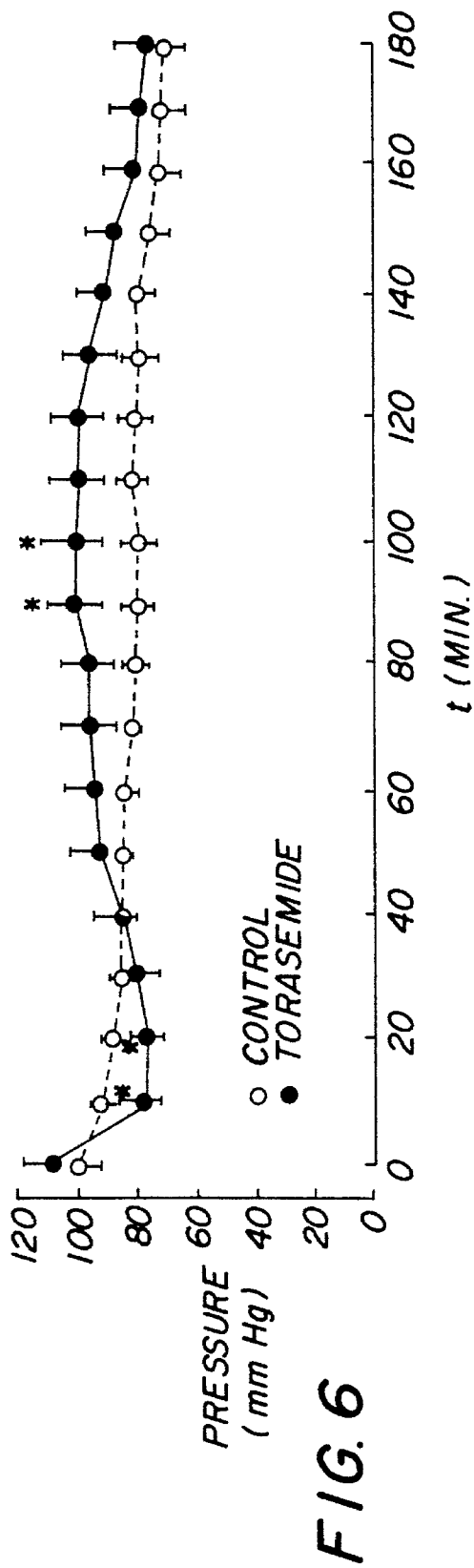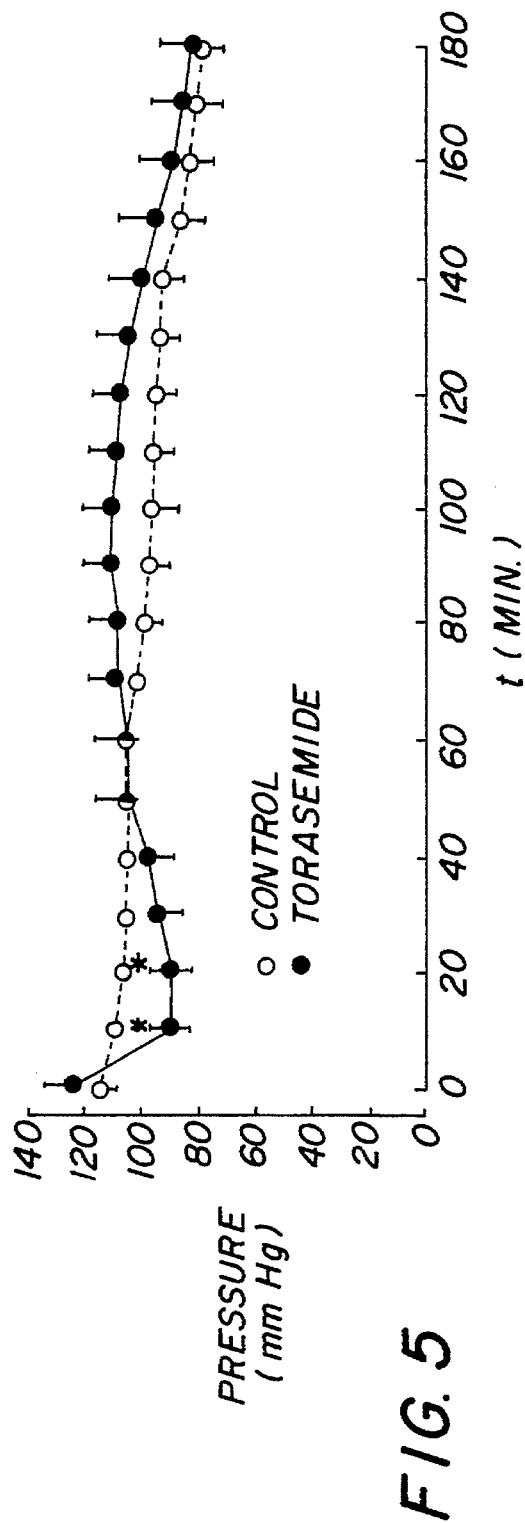

USE OF TORASEMIDE FOR THE TREATMENT OF BRAIN OEDEMAS

This application is a continuation of application Ser. No. 08/133,160 filed Oct. 21, 1993 now abandoned.

The subjects of the invention are the use of torasemide for the treatment of the swellings of nerve and glia cells in the case of brain edemas which arise as a result of e.g. skull-brain traumas and metastases and orally and parenterally administrable torasemide.

Torasemide, chemical designation 4-3'-methyl-phenylaminopyridine-3-sulphonamide, is known as loop diuretic in the case of the systemic administration of which urine volumes and electrolyte excretion increase linearly with the logarithm of the torasemide dose.

In in vitro investigations, it could be shown that torasemide clearly reduces the acidosis-induced swelling of C6 glioma cells. Furthermore, in the case of in vivo investigations on rats, it was ascertained that torasemide was able to lower the intracranial pressure (ICP) in cytotoxic brain edema initiated by hypoosmolar hyperhydration.

An acidosis occurs in the brain in the case of cerebral ischemia, in the case of skull-brain traumas, in the case of epileptic attacks, as well as under other pathophysiological conditions. In the case of cerebral ischemia, the pH value can decrease to 6.5 to 6.0, under hyperglycemic conditions the acidosis can be even more marked. As a result of the acidosis and of the reduced energy metabolism involved therewith, a net inflow of $Na^+$ and $Cl^-$ ions into the cells takes place, whereby the intracellular increase of the osmolarity leads to a corresponding water movement and thus to a cell swelling.

For diuretics such as e.g. bumetanide and furosemide which act in the kidney like torasemide via the Nacl-KCl co-transport, it was shown that they were not able to influence an experimentally increased intracranial pressure (see the article "Effect of furosemide, bumetanide and mannitol on intracranial pressure in experimental brain edema of the rat" by C. Plangger and H. Völkl in Zent bl Neurochir 50: 142–144, 1989). In this regard, it was surprising that, with torasemide, a lowering of the increased intracranial pressure could be observed.

The effectiveness of torasemide in the reduction of the swelling of glia cells or in the lowering of the ICP is shown by the investigations described in more detail in the following and illustrated by Figures.

BRIEF DESCRIPTION OF THE DRAWINGS

FIGS. 4–6 show the chronological changes of ICP in tests described herein.

FIGS. 1 and 2 show the chronological course of an in vitro acidosis-induced cell swelling of C6 glioma cells after incubation with torasemide or in the case of control experiments without verum administration. The chronological change of the vitality of the C6 glioma cells in the case of these experiments is illustrated in FIG. 3. FIGS. 4 to 6 show the chronological changes of the ICP, of the average systemic arterial blood pressure and of the cerebral perfusion pressure in rats after induction of a brain edema in two experimental series, whereby in one experimental series torasemide was administered intravenously and in the other (control) experimental series isotonic common salt solution.

In the case of the in vitro investigations concerning the influence of torasemide on acidosis-induced cell swelling, C6 glioma cells with glia-specific properties were used. The glia cells grew as monolayer in Petri dishes under conventional culture conditions with 95% ambient air, 5% $CO_2$ and at a temperature of 37° C. Culture medium was Dulbecco's minimal essential medium (DMEM) with 25 mM bicarbonate as buffer. Furthermore, the medium contained 10% fetal calf serum (FCS), as well as 100 IU/ml of penicillin G and 50 μg/ml streptomycin. For the carrying out of an experiment, the cells were harvested from 6 culture dishes with trypsin, washed twice with FCS-free medium and subsequently introduced into an experimental chamber. The chamber ensured a homogeneous stability of the individual suspension for several hours, as well as the monitoring of the medium by continuous recording of the pH value, of the oxygen partial pressure and of the temperature. The determination of the cell volume took place quantitatively with the help of a flow through cytometer according to the Coulter process. In addition, the apparatus employed hydrodynamic focussing of the particles for the improvement of the measurement exactitude. In this way, changes of the cell volume of <1% can be detected with certainty. The vitality of the cells was determined flow through-cytometrically by determination by propidium iodide. Carrying out of experiment: The cell volume, as well as the cell vitality, were first examined in a control phase (45 min) for their constant course. Furthermore, the osmolarity of the medium was determined. In addition, it was ascertained in parallel experiments that, in the case of exclusive addition of torasemide, no significant change of the cell volume and no influencing of the vitality of the C6 glioma cells took place. The cell swelling was produced after the control phase by lowering of the pH value to 6.6 or 5.0, respectively, with the help of isotonic lactic acid. The $pCO_2$ of the chamber was simultaneously increased to 80 to 100 mm Hg. The experimental period amounted to 60 minutes. In each case, 2 parallel experiments were carried out at pH 6.2 and 5.0. In the case of all but one experiment, torasemide was added to the medium in an end concentration of 1 mM 15 minutes before the acidification. The other experiment served as control.

Figure 1:
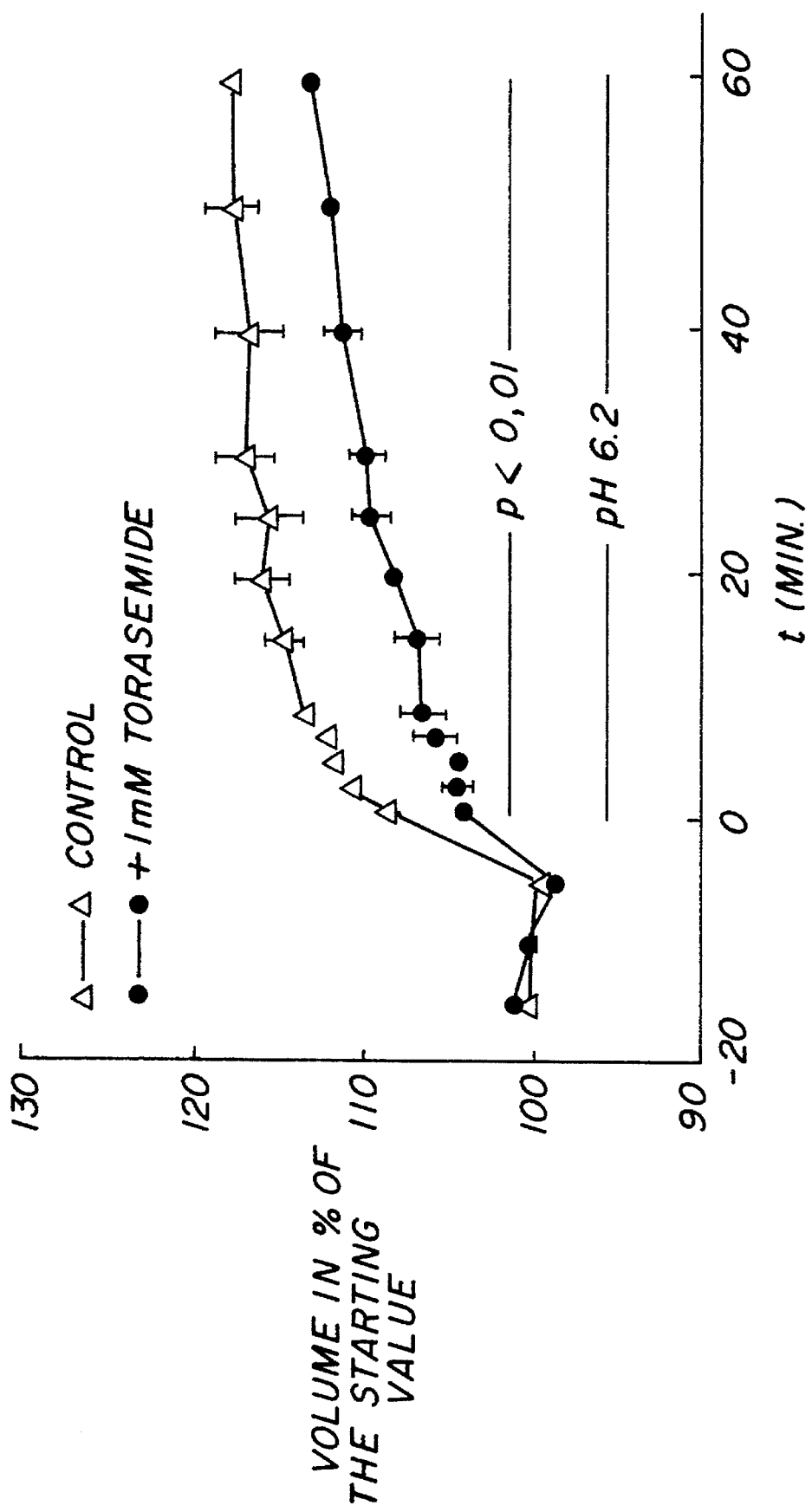
FIGS. 1 and 2 show the chronological course of an in vitro acidosis-induced cell swelling.
Figure 2:
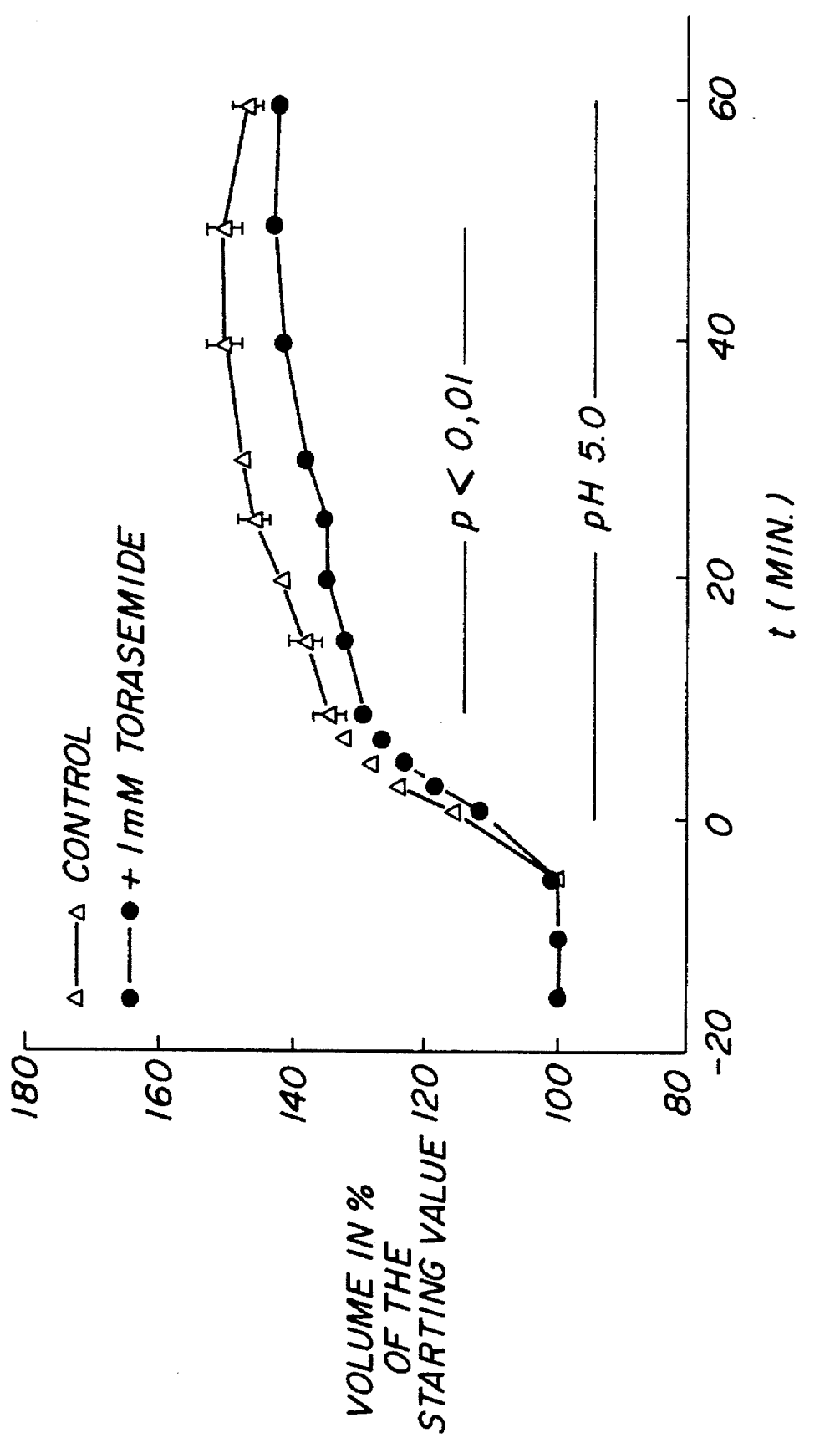
Figure 3:
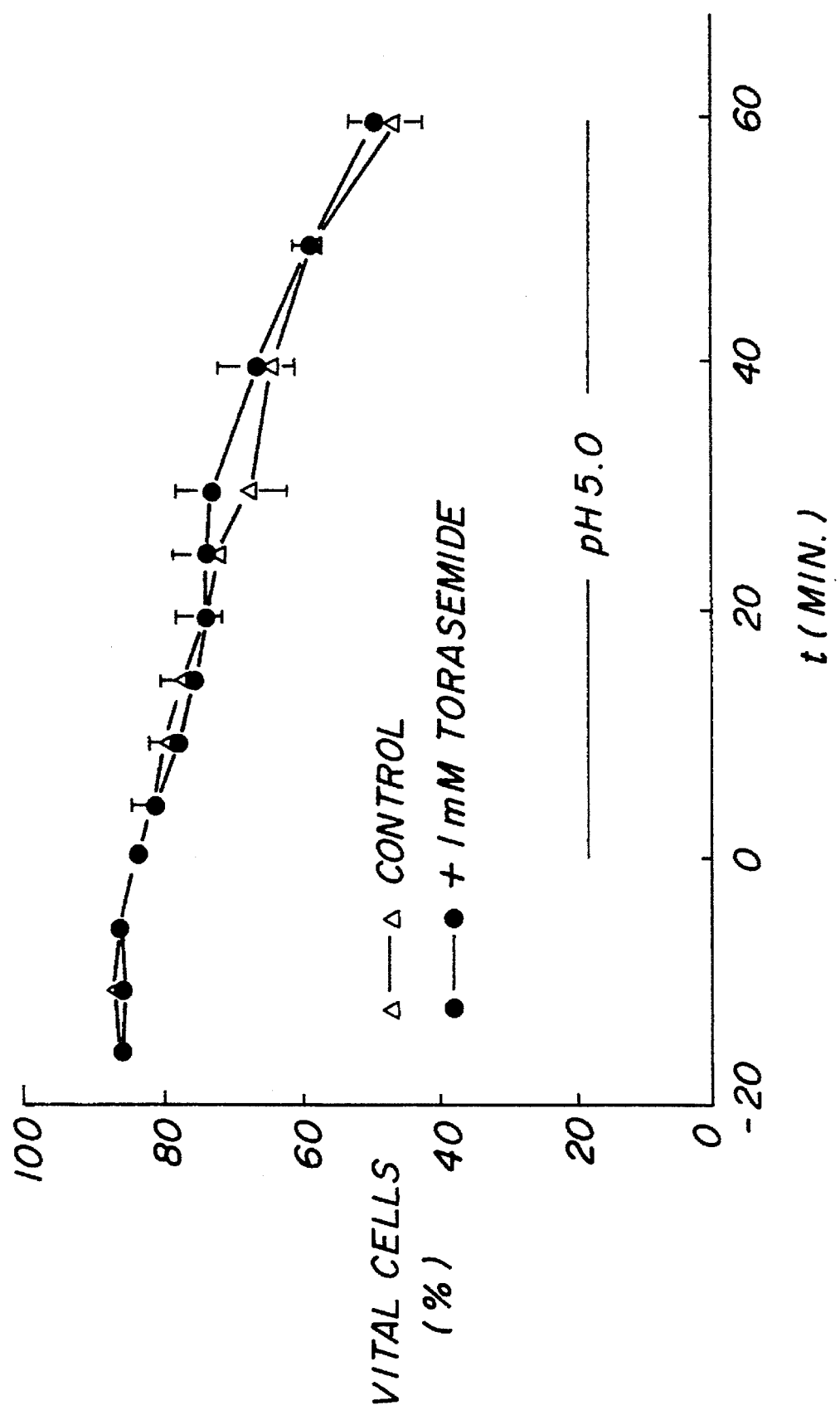
FIG. 3 is an illustration of the chronological change of the vitality of C6 glioma cells, in a test described herein.

The results are set out in FIGS. 1 and 2, in which the cell volume (in % of the starting value) is plotted against the experimental period. Furthermore, in each case the time span is given during which the pH value had sunk to 6.2 or 5.0, respectively. The time spans between the two experiments, within which the experimental data obtained under torasemide were significantly different ($p < 0.01$) from the control, are also marked. The cell volume values plotted in the curves are arithmetic averages ($\bar{x}$)± SEM. The results clearly show the inhibition of the cell swelling by torasemide. As FIG. 3 shows, torasemide furthermore has per se no influence on the vitality of C6 glioma cells. In FIG. 3 is shown the change of the vitality of the C6 glioma cells over the experimental period. Furthermore, the time span is marked during which the pH value had sunk to 5.0. One sees from the curves that admittedly the pH sinking but not the torasemide addition has an influence on the vitality. The results of the described experiments were analysed for significance with the help of the variance analysis and the Kruskal-Wallis test for the intergroup comparison.

The action of torasemide in the case of brain edema was investigated in vivo in the pharmacological model of the cytotoxic brain edema of the rat. In the case of 150 to 240 g weighted male rats, for the continuous detection of the systemic arterial blood pressure, a catheter was inserted into the right arteria femoralis and measured by means of a Gould P10 EZ blood pressure transformer, of a Siemens monitor and of a 2-canal recorder (Linseis L 650) and recorded. For the continuous detection of the ICP, a Wick catheter was introduced through a trepanation of the left front side of the skull. The ICP was measured and recorded by means of an electromagnetic Statham transformer P 23 Db, which was connected with a Hellige electromanometer, and of a 2-canal recorder (Linseis L 650). In order to exclude a possible diuretic effect, the rats were functionally nephrectomised. Carrying out the experiment: For the inducing of the brain edema, 100 ml bidistilled water/kg body weight was infused at 0.5 ml/min into the right vena jugularis. Hereafter were injected 100 mg torasemide/kg body weight in 10 ml liquid/kg body weight and in a parallel experiment 10 ml of isotonic common salt solution (placebo)/kg body weight. ICP and blood pressure were continuously recorded for 3 hours after administration of torasemide or placebo. 6 rats received a torasemide injection, 7 rats received placebo.

Figure 4:
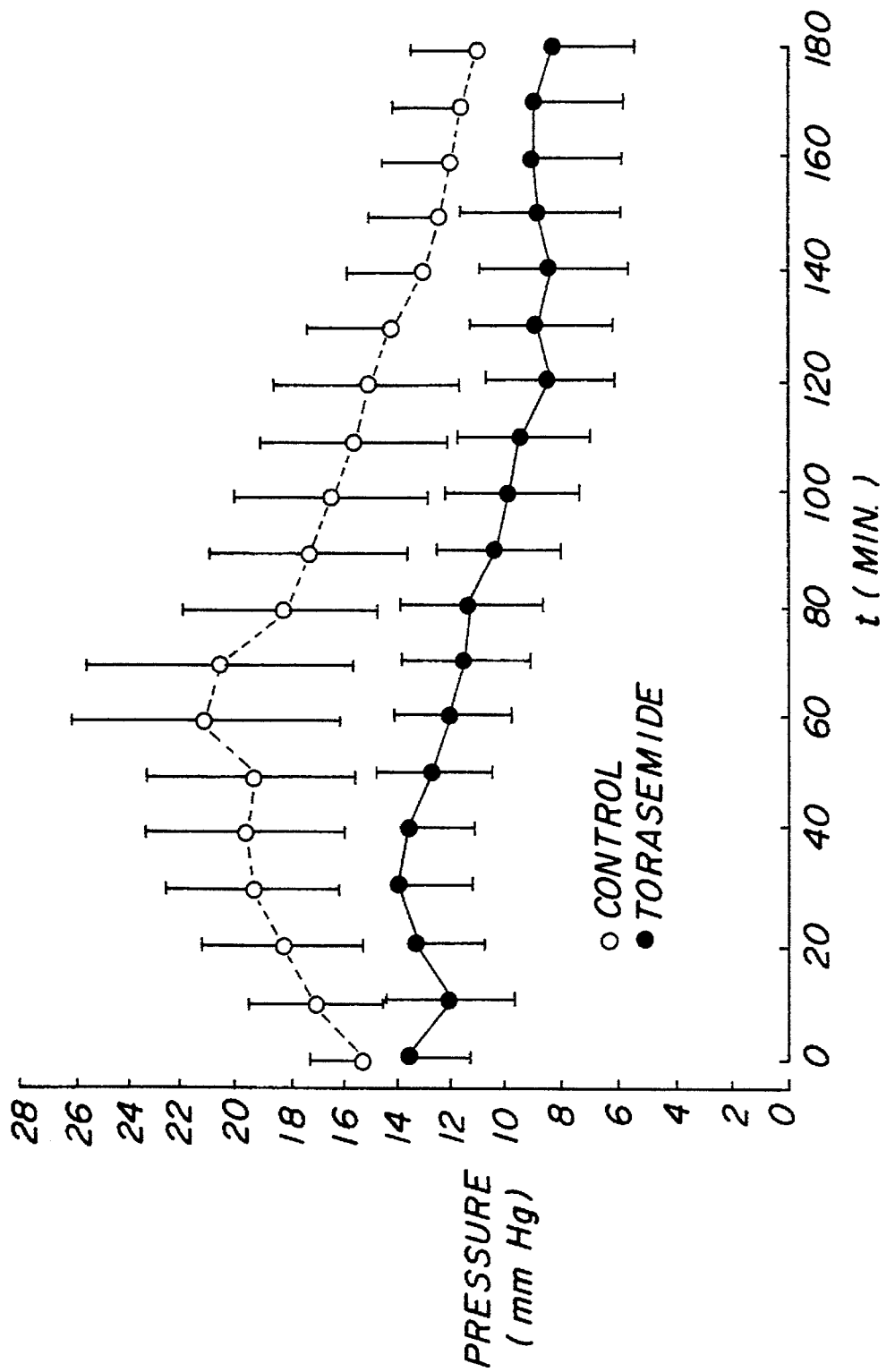

The evaluated results of the ICP and blood pressure measurements are set out in FIGS. 4 and 5, respectively. FIG. 4 shows that the CP in the case of the rats treated with torasemide was, at every point of time, lower than in the case of animals treated with placebo in the parallel experiment. However, the differences were not statistically significant. Therefore, for the verification of the finding, the cerebral perfusion pressure was also determined (the cerebral perfusion pressure is equal to the difference between the systemic average arterial blood pressure and the ICP). It was thereby found (see FIG. 6) that the values thereof 90 and 100 minutes after the administration of torasemide were significantly higher than in the control group. This was mainly to be attributed to the much lower ICP values in the rats treated with torasemide. In FIGS. 4 to 6 are plotted arithmetic average values ($\bar{x}$)± SEM against the time. The testing for significant differences between the experimental groups treated with torasemide and placebo took place by means of a one-sided Student t-test for unpaired data.

Summarising, it can be said: Not only the in vitro experiments with C6 glioma cells but also the in vivo experiments on rats show that torasemide acts swelling-inhibitingly or pressure lowering in the case of induced swelling of the glia cells and increased ICP. Torasemide is, therefore, also favorable because—as has been ascertained in experiments with C6 glioma cells (see above)—torasemide does not inpair the vitality of the glia cells; this is reduced in the same experimental procedure e.g. by amiloride. Possible causes for the pharmacological action observed with torasemide but not with e.g. furosemide and bumetanide is the high lipophilia of torasemide (octanol/$H_2O$ coefficient: 3.71).

The preparation of torasemide takes place according to the process described in the Patent Specification DE 25 16 025 C2.

On the basis of its high bioavailability, torasemide can be used in equivalent doses not only orally but also parenterally for the therapy of brain edemas of various genesis.

For the preparation of medicaments to be administered orally, torasemide is mixed in per se known manner with suitable pharmaceutical carrier substances, aroma, flavoring and coloring materials and formed, for example, as tablets or dragees or, with the addition of appropriate adjuvants, suspended or dissolved in water or oil, such as e.g. olive oil.

For the production of a pharmaceutical preparation to be administered parenterally, torasemide, possibly in the form of its pharmacologically acceptable salts, is suspended or dissolved in water in per se known way with addition of appropriate adjuvants, such as e.g. emulsifiers.

Torasemide is administered in amounts between 5 and 40 mg per day.

An exemplary formulation for a tablet with 10 mg of active material is composed as follows:

| | |
|---|---|
| torasemide | 10.0 mg |
| lactose.1 $H_2O$ | 116.0 mg |
| maize starch | 32.0 mg |
| colloidal silicon dioxide | 1.2 mg |
| magnesium stearate | 0.4–1.0 mg |
| weight of a tablet | 159.6–160.2 mg |

An exemplary formulation for a pharmaceutical preparation to be administered parenterally with 10 mg of active material is composed as follows:

| | |
|---|---|
| sodium torasemide | 10.631 mg |
| sodium hydroxide | 0.05 mg |
| trometamol (2-amino-2-hydroxymethyl-1,3-propanediol) | 0.25 mg |
| macrogol (polyethylene glycols) | 225.00 mg |
| water | 1804.069 mg |
| nitrogen | q.s. |

We claim:

1. A method of treating a brain edema in a patient in need of such treatment, said method comprising administering to said patient an effective amount of 4-3'-methylphenylaminopyridine-3-sulphonamide or a pharmacologically acceptable salt thereof.

2. Method of claim 1, wherein the brain edema occurred as a result of severe skull-brain trauma, cerebral ischemia, stroke, metastases or an epileptic fit.

3. Method of claim 1, wherein the brain edema is a cytotoxic brain edema initiated by hypoosmolar hyperhydration.

4. Method of claim 1, wherein the amount is from 5 to 40 mg per day.

5. A method of reducing the swellings of nerve and glia cells and/or reducing intracranial pressure caused by a brain edema in a patient in need of such treatment, said method comprising administering to said patient an effective amount of 4-3'-methylphenylaminopyride-3-sulphonamide or a pharmacologically acceptable salt thereof.

6. Method of claim 5, wherein the brain edema occurs as a result of severe skull-brain trauma, cerebral ischemia, stroke, metastases or an epileptic fit.

7. Method of claim 5, wherein the brain edema is a cytotoxic brain edema initiated by hypoosmolar hyperhydration.

8. Method of claim 5, wherein the amount is from 5 to 40 mg per day.

* * * * *